United States Patent [19]

Nakanishi et al.

[11] Patent Number: 4,636,464

[45] Date of Patent: Jan. 13, 1987

[54] PYRANOSE OXIDASE, METHOD OF MAKING AND METHOD OF USE

[75] Inventors: Toru Nakanishi, Atsugi; Yozo Machida, Yokohama, both of Japan

[73] Assignee: Kyowa Hakko Kogyo Co., Ltd., Tokyo, Japan

[21] Appl. No.: 764,960

[22] Filed: Aug. 12, 1985

Related U.S. Application Data

[63] Continuation of Ser. No. 474,310, Mar. 11, 1983, abandoned.

[51] Int. Cl.$^4$ .............................. C12Q 1/54; C12N 9/04
[52] U.S. Cl. ........................................ 435/14; 435/190
[58] Field of Search ................................. 435/14, 190

[56] References Cited

U.S. PATENT DOCUMENTS

| | | | |
|---|---|---|---|
| 3,930,953 | 1/1976 | Stark | 435/190 |
| 4,321,323 | 3/1982 | Maselli et al. | 435/190 |
| 4,440,855 | 4/1984 | Horwath et al. | 435/190 |
| 4,442,207 | 4/1984 | Horwath et al. | 435/190 |

FOREIGN PATENT DOCUMENTS

0054358 6/1982 European Pat. Off.
81/03666 12/1981 PCT Int'l Appl.

OTHER PUBLICATIONS

Janseen, F. W. et al; "Carbohydrate Oxidase . . . ", Biochim. Biophys. ACTA., vol. 167, (1968), pp. 501–510.

Volc, J., et al; "Glucose-2-Oxidase . . . ", Folia Microbiol., vol. 23, (1978), pp. 292–298.

ATCC Catalogue of Strains I, 15th Ed., (1982), pp. 338, 463.

Chemical Abstracts, vol. 99, No. 1, Jul. 4, 1983, p. 392, No. 4091x.

*Primary Examiner*—Sam Rosen
*Attorney, Agent, or Firm*—Fitzpatrick, Cella, Harper & Scinto

[57] ABSTRACT

A novel pyranose oxidase exhibiting the strong specific activity only on glucose is produced by fermentation of a microorganism of the genus Coriolus, Daedaleopsis, Gloeophyllum or Pleurotus. The enzyme is useful for the determination of glucose.

16 Claims, 5 Drawing Figures

PYRANOSE OXIDASE, METHOD OF MAKING AND METHOD OF USE

This application is a continuation of application Ser. No. 474,310, filed Mar. 11, 1983 now abandoned.

BACKGROUND OF THE INVENTION

The present invention relates to pyranose oxidase exhibiting a strong specific activity on glucose, a process for production thereof, a method for the determination of the substrate for pyranose oxidase and a test composition suitable therefor.

Pyranose oxidase (EC 1.1.3.10) is an enzyme which catalyzes the reactions wherein glucose, xylose and sorbose are oxidized into glucosone, xylosone and 5-ketofructose, respectively [Methods in Enzymol, vol. XLI, p.170, (1975)]. In oxidizing these substances, oxygen is consumed and hydrogen peroxide is formed.

The enzyme is, therefore, useful for the determination of pyranose such as glucose, xylose, sorbose, etc. in a sample.

Heretofore, it is well known that pyranose oxidase is produced by culturing a microorganism belonging to the genus Polyporus [Methods in Enzymol, Vol. XLI p.170 (1975)].

The known enzyme exhibits the specific activity on not only glucose but also xylose and sorbose.

As a result of studies about fermentation process for production of pyranose oxidase, it has been found that a microorganism belonging to the genus Coriolus, Daedaleopsis, Pleurotus or Gloeophyllum produces novel pyranose oxidase exhibiting the strong specific activity on glucose.

SUMMARY OF THE INVENTION

According to the present invention, the novel pyranose oxidase is obtained by culturing a microorganism belonging to the genus Coriolus, Daedaleopsis, Gloeophyllum or Pleurotus and capable of producing the novel pyranose oxidase in a nutrient medium until enzymatic activity is detected in the culture liquor and thereafter recovering the pyranose oxidase therefrom.

The enzyme is useful for the determination of the substrate for pyranose oxidase, especially D-glucose. That is, the substrate for pyranose oxidase is determined by oxidizing the substrate with the novel pyranose oxidase in the presence of oxygen and determining the amount of the reaction product or the amount of oxygen consumed by said reaction.

DESCRIPTION OF THE INVENTION

Pyranose oxidase of the present invention has the enzymological properties determined as follows.

The assay method for enzymatic activity are as follows.

[Assay Method for Enzymatic Activity]

The enzymatic activity of pyranose oxidase is most conveniently assayed in the following manner. At first, 3.0 ml of the enzyme-containing solution comprising 1.0 ml of 0.1M tris-hydrochloride buffer (pH 7.0), 0.2 ml of a coloring reagent prepared in advance as hereinafter described, 0.1 ml of 1M glucose solution, 0.1 ml of a pyranose oxidase solution, 0.1 ml of 0.1 mM flavinadenine dinucleotide and 1.5 ml of distilled water is incubated at 37° C. Said coloring reagent is prepared by adding 0.1M tris-hydrochloride buffer (pH 7.0) containing 10 m mol/l 4-aminoantipyrine (hereinafter referred to as 4AA) and 10 m mol/l phenol, to peroxidase in a concentration of 2000 U per 100 ml of the buffer. The increasing rate of the absorbancy at 500 nm is automatically measured on a spectrophotometer. The molecular extinction coefficient of a quinoneimine pigment formed under these conditions is defined as $5.3 \times 10^3$, and one unit of the enzymatic activity is also defined as the amount of the enzyme that produces one $\mu$ mole of hydrogen peroxide per minute at a temperature of 37° C. and at a pH of 7.0. The enzymatic activity of pyranose oxidase (A) can be calculated from:

$$A = \frac{\Delta A_{500}}{5.3} \times \frac{3.0}{0.1} \times \text{the dilution rate of the enzyme}$$

$\Delta A_{500}$: the increasing rate of the absorbancy at 500 nm per minute

[Properties of pyranose oxidase]

(1) Stable pH range

The enzyme preparate is dissolved in various buffer solutions having the pH indicated in FIG. 1 to make up enzyme solutions having an activity of 100 mU/0.7 ml. As buffer solutions, citrate buffer, Tris buffer and borate buffer are used. Each enzyme solution is incubated at 50° C. for 30 minutes, cooled and neutralized to measure the residual enzymatic activity.

The present enzyme is stable at a pH of 5.0–7.4 as shown in FIG. 1.

(2) Optimum pH

The enzyme preparate is dissolved in Tris buffer solutions having the pH indicated in FIG. 2 to make up enzyme solutions having an activity of 250 mU/3.7 ml. Each of the enzyme solution is put into a flask of BIOXYGRAPH (trade name for cell for measuring oxygen made by Kyusui Kagaku Laboratory, Japan), and 50 $\mu$l of 1M glucose is added thereto to determine the amount of absorbed oxygen. The optimum pH for this enzyme is determined to be around 6.2.

(3) Optimum temperature

The same enzymatic reactions as described in assay method for enzymatic activity are repeated for 5 minutes at the temperatures indicated in FIG. 3 except that 100 mU of pyranose oxidase is used. The optimum temperature for the present enzyme is determined to be 50° C.

(4) Heat stability

The enzyme preparate is dissolved in 0.6 ml of 0.2M Tris buffer solution (pH 6.0) to make up an enzyme solution having an activity of 100 mU/0.7 ml. The enzyme solution is incubated for 30 minutes at the temperatures indicated in FIG. 4 to measure the residual enzymatic activity. This enzyme keeps 90% of its activity with treatment at 60° C. for 30 minutes.

(5) Substrate specificity

The same enzymatic reaction as described in assay method for enzymatic activity are repeated except that 2.5 U pyranose oxidase and as the substrate, 0.1 ml of 100 mM various carbohydrate liquors indicated in Table 1 are used. The results are expressed as percentages of the glucose reaction. The specificity of this enzyme with glucose is high. This enzyme acts upon sorbose and xylose.

TABLE 1

| Substrate | Relative Activity (%) | Substrate | Relative Activity (%) |
|---|---|---|---|
| glucose | 100 | maltose | 0 |
| mannose | 0.9 | trehalose | 0 |
| galactose | 0.9 | lactose | 0 |
| sorbose | 3.4 | mannitol | 0 |
| fructose | 0 | glucosamine | 0 |
| xylose | 2.6 | gluconic acid | 0 |

The specificity of this enzyme with sorbose and xyrose is a great deal lower than that of heretofore known pyranose oxidase derived from a microorganism belonging to the genus Polyporus [Table 1 of B. B. A. 167, 501–510 (1968)].

(6) Electron acceptor

In this phase, 1.4 ml of 50 mM tris-hydrochloride buffer (pH 7.0), 0.1 ml of 250 mU enzyme solution and 0.5 ml of electron acceptor solutions having various concentrations as indicated in Table 2 are put into a cell with Thunberg tube. After sucking dissolved oxygen removed, the reaction solution is mixed with 0.5 ml of 0.1M glucose solution. The change in absorbancy per minute from 30 minutes to 90 minutes after the mixturing is determined and the activities of the electron acceptors are expressed as relative activity. The optimum electron acceptor for this enzyme is oxygen and 2,6-dichlorophenolindophenol and cytochrome C may be made electron acceptor.

TABLE 2

| Electron Acceptor | Concentration (mM) | Relative Activity (%) |
|---|---|---|
| Oxygen | Dissolved | 100 |
| 2,6-Dichlorophenolindophenol | 0.04 | 2.5 |
| Nitroprusside-tetrazolium | 0.1 | 0 |
| Cytochrome C | 0.1 | 0.33 |
| Nicotinamide-adenine dinucleotide | 0.1 | 0 |
| Nicotinamide-adenine dinucleotide phosphate | 0.1 | 0 |
| Ferricyanide compound | 0.5 | 0 |

(7) Inhibitor

The inhibitor is studied in the same manner as that adopted in determination of the optimum pH. A reaction solution comprising 3.4 ml of 50 mM tris-hydrochloride buffer (pH 7.0), 0.1 ml of enzyme solution containing 280 mU of pyranose oxidase and 0.2 ml of 18.5 mM inhibitor solution is put into a cell for measuring oxygen and 50 μl of 1 M glucose is added thereto and incubated at 37° C. The results are given in Table 3. The enzymatic action is inhibited by $Cu^{2+}$, $Ag^+$, $Ni^{2+}$ and p-chloromercuribenzoate.

TABLE 3

| Inhibitor | Percent Inhibition (%) |
|---|---|
| magnesium sulfate | 0 |
| cobalt sulfate | 13.3 |
| copper sulfate | 35.7 |
| silver nitrate | 53.3 |
| nickel chloride | 28.6 |
| 8-hydroxyquinoline | 13.3 |
| hydrogen peroxide | 20.0 |
| p-chloromercuribenzoate | 50.0 |

(8) Isoelectric point

The isoelectric point for this enzyme is 4.2 according to the isoelectric focucing method using carrier ampholyte at a pH of 3.5–10.0.

(9) Molecular weight

As the standard protein, egg albumin, bovine blood serum, alcohol dehydrogenase, γ-globulin and xanthin oxidase derived from milk are used.

The molecular weight of this enzyme is calculated to be about 220,000 by Sephadex G-200 gel-filtration method.

(10) Km value

According to the Lineweaver-Burk plot method using 2.5 U pyranose oxidase the Km value for glucose is determined to be 0.83 mM, which is about one-twelfth to one-twenty fourth of that of glucose oxidase (10–20 mM).

Pyranose oxydase of the present invention is produced as follows.

Any microorganism may be used in the present invention so long as it belongs to the genus Coriolus, Daedaleopsis, Pleurotus or Gloeophyllum and is capable of producing pyranose oxidase. Examples of the preferred strains are *Coriolus versicolar* ATCC 20155, *Daedaleopsis styracina* ATCC 20188, *Gloeophyllum sepiarium* Z-41, NRRL 12506 and *Pleurotus ostreatus* Z-64, NRRL 12507.

These strains have been deposited with American Type Culture Collection in U.S.A or Northern Regional Research Laboratory in U.S.A and are available to the third parties.

The mycological properties of the strain are described in the following literature.

| | |
|---|---|
| *Coriolus versicolor* *Daedaleopsis styracina* *Gloeophyllum sepiarium* *Pleurotus ostreatus:* | Nihon Kinrui Shi (Japanese Microorganisms) Vol. 4, No. 2, (1955) by Seiya Ito Genshoku Nihon Kinrui Zukan (Primary Color Japanese Microorganism Pictorial Book) (1957) by Imazeki and Hongo |

Either a synthetic or natural medium may be used as long as it properly contains a carbon source, a nitrogen source, minerals and other nutrients.

As the carbon source, various carbohydrates such as glucose, fructose, sucrose, maltose, mannose, starch, starch hydrolyzate liquor, molasses, etc., various sugar alcohols such as glycerol, sorbitol, mannitol, etc., various organic acids such as acetic acid, lactic acid, pyruvic acid, fumalic acid, citric acid, etc., various alcohols such as methanol, ethanol, etc., various glycols such as ethylene glycol, propylene glycol, etc., various amino acids, and hydrocarbons such as n-hexadecane, etc., may be used.

As the nitrogen source, there may be employed ammonia, various inorganic and organic ammonium salts such as ammonium chloride, ammonium carbonate, ammonium phosphate, ammonium nitrate, ammonium acetate, etc., urea, amino acids and other nitrogen-containing compounds, as well as nitrogenous organic materials such as peptone, NZ-amine, meat extract, corn steep liquor, casein hydrolyzate, chrysalis hydrolyzate, fish meal, its digest product, defatted soybean, its digest product, etc.

As the minerals, appropriate are potassium primary phosphate, potassium secondary phosphate, potassium chloride, magnesium sulfate, manganese sulfate, ferrous sulfate, sodium chloride, calcium carbonate, etc.

Culturing is carried out with aeration and stirring at a pH of 3.0–8.0 and at a temperature of 20°–35° C. for 1–7 days.

Culturing is continued until the enzymatic activity is detected in the culture liquor, mostly within the microbial cells, generally for 2–4 days. Recovering of pyranose oxidase from the culture liquor is carried out as follows:

After completion of culturing, the microbial cells are collected from the culture liquor by filtration and disrupted by suitable means to obtain a cell extract. The extract is subjected to centrifugation to obtain a supernatant. Then, the supernatant is subjected to conventional purification methods such as salting-out, precipitation with organic solvent, dialysis, ion exchange cellulose column chromatography, gel-filtration method and freeze-drying. Thus, purified pyranose oxidase can be recovered.

Basically, the method and test composition according to the present invention for the determination of the substrate for pyranose oxidase in a sample comprise a system (A) for oxidizing the substrate with the novel pyranose oxidase and a system (B) for determining the reaction product or the amount of oxygen consumed in the enzymatic reaction.

The present invention is based on the following principle. When the substrate for pyranose oxidase is oxidized by the action of pyranose oxidase, the amount of the reaction product or the amount of consumed oxygen is directly proportional to the amount of the substrate in a sample.

Since the present enzyme exhibits a strong specific activity only on glucose, it is useful for the determination of glucose.

Where the substrate is glucose, the enzyme reaction is schematically below.

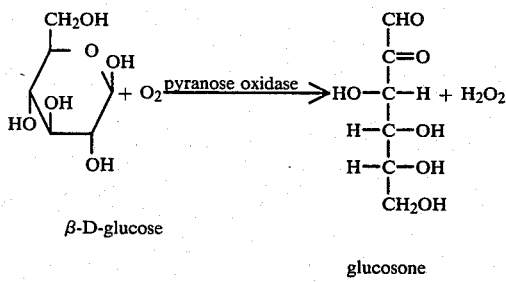

The present invention can be applied to the determination of the compound which participates in the reaction system wherein the substrate for pyranose oxidase is quantitatively formed by the reaction or decomposition and the determination of the activity of enzyme which catalyzes the reaction in the system. Examples of the compound or the enzyme which can be determined by the present invention include glucose derivatives such as maltose, methyl glucoside, enzymes such as glucosidase, maltose phosphoryrase, malate dehydrogenase, glucose-6-phosphatase, amylase, glucose-1-phosphatase, trehalase, reduced nicotinamide-adeninedinucleotide (phosphate) [NAD(P)H$_2$] and ADP.

The enzymatic reaction for the determination of these compounds or enzymes are shown below.

(1) For amylase, maltose, maltosephosphorylase (MPR)

(1) For amylase, maltose, maltosephosphorylase (MPR)

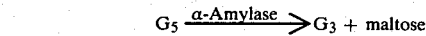

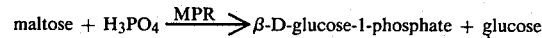

↓

Detection (2) For NAD(P)H$_2$

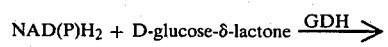

NAD(P) + β-D-glucose

↓

Detection

GDH: glucose dehydrogenase (3) For malate dehydrogenase (MDH)

↓

Detection (4) For ADP

ATP + D-glucose

↓

Detection (5) For glucose-6-phosphatase (G6P)

(6) For glucose-1-phosphatase (G1P)

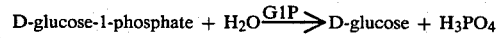

(7) For trehalase

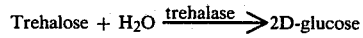

According to the present invention, the determination of the substrate may be performed by conducting the individual systems stepwise and may preferably be performed by subjecting the sample to enzymatic reaction and a color-forming reaction with a reagent comprising pyrarose oxidase and a detecting system for at least one of the products formed by the enzymatic reaction. An example of a preferred detecting system is hydrogen peroxide detecting system which comprises peroxidase and a chromogen.

Several methods for the determination of hydrogen peroxide are known. Representative methods include:

(1) reacting hydrogen peroxide with a chromogen in the presence of peroxidase to form a pigment and determining the pigment colorimetrically;

(2) reacting hydrogen peroxide with alcohol in the presence of catalase to form an aldehyde, reacting the aldehyde with acetyl acetone and ammonia to form a pigment and determining the pigment colorimetrically; and (3) reacting hydrogen peroxide with alcohol in the presence of catalase to form an aldehyde, reacting the aldehyde with the reduced form of nicotineamide adenine dinucleotide (hereinafter referred to as NADH) to form nicotineamide adenine dinucloeotide (hereinafter referred to as NAD) and determining NAD colorimetrically.

Among these methods, the method using peroxidase is very simple and the determination of hydrogen peroxide is performed by measuring the absorbancy of the reaction solution based on the color development of formed pigment with a spectrophotometer.

In determining a substrate for pyranose oxidase, a sample containing the substrate and pyranose oxidase are added to an appropriate buffer at a pH of 7.0–8.0 and the mixture is subjected to reaction. Pyranose oxidase may be microencapsulated or immobilized by a carrier, if necessary.

As a buffer solution, borate buffer, phosphate buffer, tris-hydrochloride buffer, tris-maleate-hydrooxide buffer, citrate-disodium phosphate buffer, succinate-borate buffer, phosphate-borate buffer and the like are used in a concentration of 0.005–0.5 mol/l. The enzyme is generally used in a concentration of 0.1–10 U/ml.

Examples of chromogen are 4-aminoantipyrine (4AA) -phenol, 4AA-dimethylaniline (DMA), 4AA-diethylaniline (DEA), 4AA-N-ethyl-N-meta-methylphenyl-N'-acetylethylenediamine (EMAE), 3-methyl-2-benzothiazoline-hydrazone-HCl (MBTH)-phenol, MBTH-DEA, 4AA-dibutylaniline (DBA), MBTH-DBA, 4AA-3,5-dimethoxy-N-($\beta$-hydroxy-$\gamma$-sulphopropyl)-aniline (DHSA), etc.

Reaction is carried out in the presence of peroxidase and a chromogen in a concentration of 0.5–10 U/ml and 1–20 $\mu$mol/ml, respectively, at a temperature of 30°–50° C., and continued for 5–20 minutes. After completion of the enzymatic reaction, the absorbancy of the reaction solution is measured at a visible ray region, generally at 400–600 nm. The relationship between the amount of a substrate and the absorbancy is given in advance in the form of calibration curve prepared using a standard solution of the substrate. Then, the substrate contained in a sample is determined from the absorbancy of the sample.

The present invention also relates to a test composition for determination and a kit utilizing thereof. The test composition comprises the novel pyranose oxidase, peroxidase and a chromogen and the kit is made of the test composition and a buffer solution. The test composition may contain an enzyme or decomposition reagent necessary for forming glucose. For example, a test composition for determining $\alpha$-amylase contains starch and maltose phosphorylase.

Figure 1:
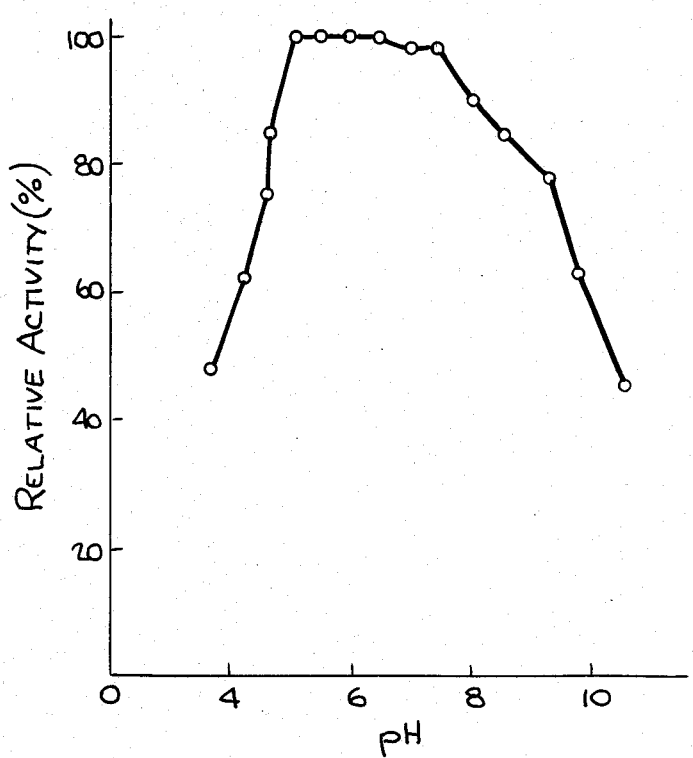
FIG. 1 shows the relationship between the relative activity of pyranose oxidase and the stable pH range.
Figure 2:
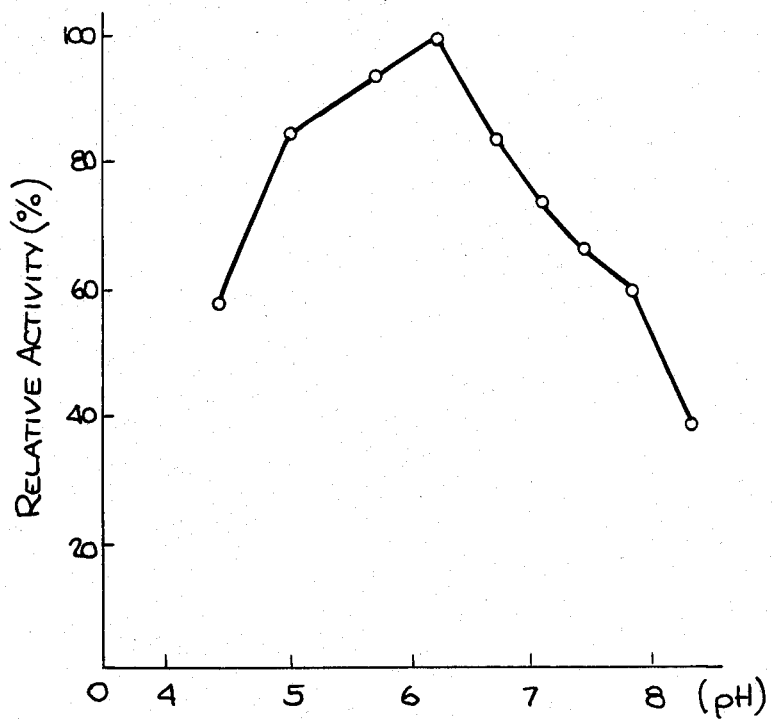
FIG. 2 shows the relationship between the relative activity of pyranose oxidase and the optimum pH.
Figure 3:
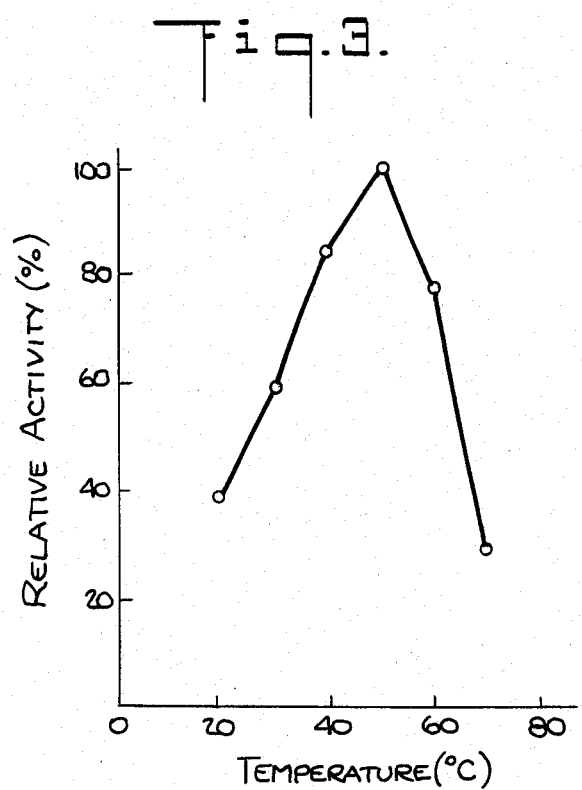
FIG. 3 shows the relationship between the relative activity of pyranose oxidase and the optimum temperature.
Figure 4:
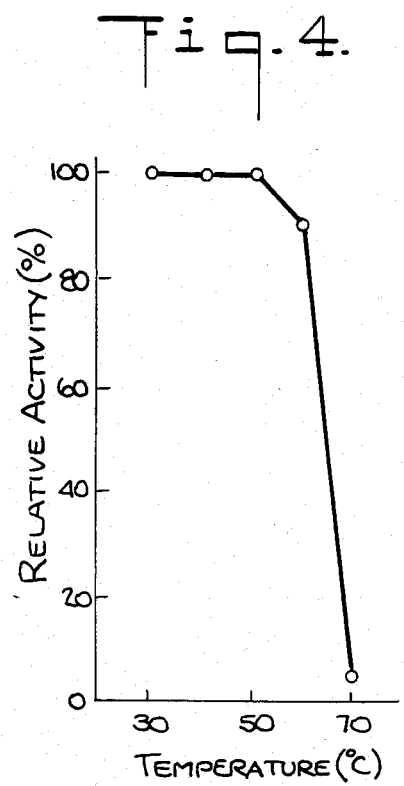
FIG. 4 shows the relationship between the relative activity of pyranose oxidase and the heat stability.

Certain specific enbodiments of the present invention are illustrated by the following representative examples.

EXAMPLE 1

In this example, 30 ml of a seed medium (pH 6.0) comprising 0.5 g/dl glucose, 0.4 g/dl yeast extract, 1 g/dl malt extract and 1 mg/dl ferric chloride is put into a 300 ml-Erlenmeyer flask and sterilized at 120° C. for 15 minutes. One loopful of *Coriolus versicolor* ATCC 20155 is inoculated into the seed medium and cultured with shaking at 30° C. for 5 days. Then, 30 ml of the seed culture liquor thus obtained is put into a 2 l-Erlenmeyer flask containing 300 ml of a culture medium comprising the same components as the first seed medium and cultured with shaking at 30° C. for 4 days. Thereafter, 1.2 l of the second seed culture liquor is poured into a 30 l-jar fermenter containing 18 l of a fermentation medium comprising the same components as the seed medium. Main fermentation is carried out with aeration-stirring at an aeration rate of 1 l/min., a stirring speed of 250 rpm and 30° C. for 2 days. The enzymatic activity of pyranose oxidase contained in the resulting culture liquor is 161 mU based upon 1 ml of the culture liquor. After the completion of culturing, the culture liquor is subjected to filtration by means of suction, whereby 1 kg (wet weight) of microbial cells is obtained. The cells are suspended in 1.8 l of 50 mM tris-hydrochloride buffer (pH 7.0) (the buffer solutions used hereinafter are the same as this buffer) and then disrupted by homogenizer. The disrupted cells are centrifuged to obtain 1.8 l of supernatant. The supernatant is adjusted to pH 7.0 while adding alkali thereto and passed through a column of one l of HPA-75 pre-equilibrated with the buffer (product of Mitsubishi Kasei Co., Ltd., Japan). After the column is washed with the buffer and successively with the buffer containing 0.1M ammonium sulfate, elution is carried out with the buffer containing 0.25M ammonium sulfate. The active fractions of the enzyme are combined and mixed with ammonium sulfate to 80% saturation. The formed precipitate is recovered by centrifugation and dissolved in 30 ml of the buffer. Then, the resulting solution is charged on a column of one l of Sephalose 4B and elution is carried out with the buffer. The active fractions of the enzyme are combined and mixed with ammonium sulfate to 80% saturation. The formed precipitates is recovered by centrifugation and dissolved in 30 ml of the buffer. The resulting enzyme solution is again passed through a column of 500 ml of Sephadex G-100, and elution is carried out with the buffer. The active fractions are freeze-dried whereby 815 mg of an enzyme preparate is obtained (specific activity: 9.6 U/mg protein). The yield in terms of activity based on the supernatant obtained by eluting the disrupted cell suspension is 43%.

EXAMPLE 2

In this example, *Gloeophyllum sepiarium* Z-41 is inoculated into the medium having the same composition as that of the medium prepared in Example 1 in a 2 l-Erlenmeyer flask and cultured for 6 days. The enzymatic activity of pyranose oxidase contained in the resulting culture liquor is 365 mU/ml.

EXAMPLE 3

The same culturing as in Example 1 is carried out except that *Daedaleopsis styracina* ATCC 20188 is used as a seed strain. The enzymatic activity of pyranose oxidase contained in the resulting culture liquor is 189 mU/ml.

EXAMPLE 4

The same culturing as in Example 1 is carried out except that *Pleurotus ostreatus* Z-64 is used as a seed strain. The enzymatic activity of pyranose oxidase contained in the resulting culture liquor is 59 mU/ml.

Figure 5:
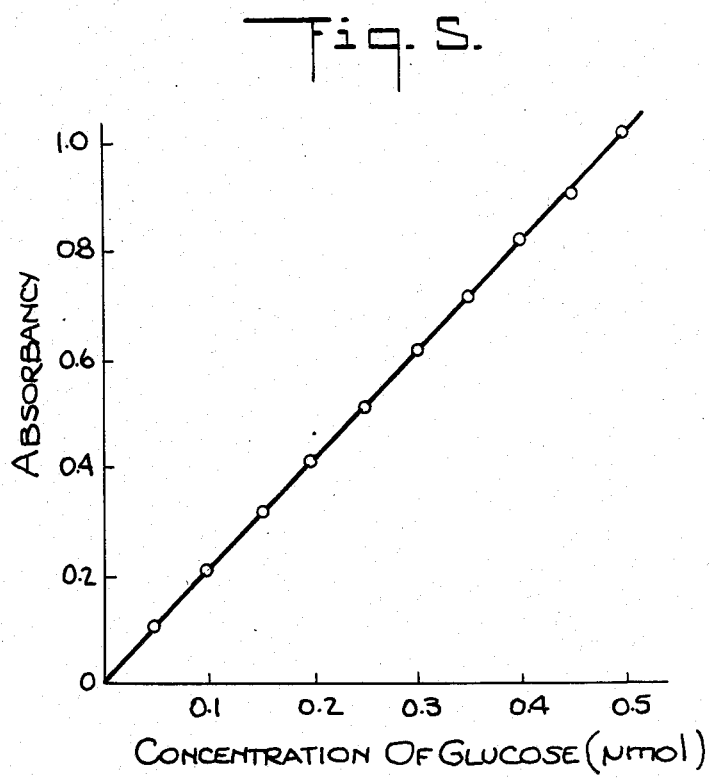
FIG. 5 shows the relationship between the absorbancy and the glucose concentration.

EXAMPLE 5 To 0.2 ml of a solution containing glucose in each of concentrations indicated at the measured points of FIG. 5, are added 1.5 ml of 0.1M potassium phosphate buffer (pH 7.5), 0.2 ml of a coloring reagent solution (pH 7.5) containing 10 mmol/l 4AA, 10 mmol/l phenol and 20 U/ml, 0.1 ml of 0.1 mM FAD and 1 ml of a pyranose oxidase solution (6.7 U) to make up 3.0 ml of a reaction solution. The enzymatic reaction solution is incubated at 37° C. for 10 minutes. Then, the absorbancy of the solution is measured at 500 nm, the result of which is shown in FIG. 5. Proportional relationship between the glucose concentrations and the absorbancies is recognized.

EXAMPLE 6

| Determination of glucose | | |
|---|---|---|
| Reagent 1 | Ascorbate oxidase | 5 U/ml |
| | Triton X-100 | 0.15% |
| | Adekatol LO-5 | 0.075% |
| | DHSA | 0.4 mg/ml |
| | 50 mM Borax-100 mM KH$_2$PO$_4$ | (pH 6.5) |
| Reagent 2 | 4AA | 0.15 mg/ml |
| | Peroxidase | 7 U/ml |
| | Pyranose oxidase | 3.5 U/ml |
| | Triton X-100 | 0.15% |
| | Adekatol LO-5 | 0.075% |
| | HCl—semicarbazide | 0.4 mg/ml |
| | 50 mM Borax-100 mM KH$_2$PO$_4$ | (pH 6.5) |

Procedure

Test tube
    |← 1.5 ml of Reagent 1
    |← 20 μl of Serum sample, Standard solution or Distilled water
Pre-incubation (37° C., 5 min)
    |← 1.5 ml of Reagent 2

Incubation (37° C., 5 min)
|
Measurement of absorbancy of the solution at 585 nm (E) (Control: Distilled water)

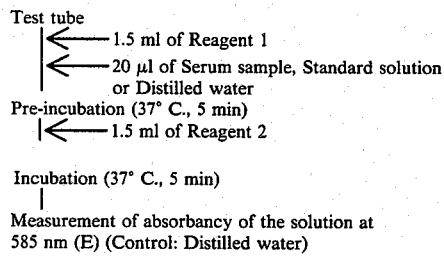

$$G\ (mg/dl) = \frac{E_S - E_W}{E_{ST} - E_W} \times C\ (mg/dl)$$

G: glucose concentration in sample
E$_S$: absorbance value of sample
E$_{ST}$: absorbance value of standard solution
E$_W$: absorbance value of distilled water
C: concentration of standard solution Results

| | ΔE | G (mg/dl) |
|---|---|---|
| Standard solution (200 mg/dl) | 0.459 | — |
| Sample No. 1 | 0.652 | 284 |
| Sample No. 2 | 1.074 | 468 |
| Sample No. 3 | 0.681 | 297 |

| -continued | | |
|---|---|---|
| Determination of glucose | | |
| Sample No. 4 | 0.976 | 425 |
| Sample No. 5 | 0.505 | 220 |
| Sample No. 6 | 0.311 | 136 |
| Sample No. 7 | 0.793 | 346 |
| Sample No. 8 | 0.222 | 97 |
| Sample No. 9 | 0.150 | 65 |
| Sample No. 10 | 0.178 | 78 |

EXAMPLE 7

| Determination for amylase | | |
|---|---|---|
| Reagent 1 | EMAE | 1.2 mg/ml |
| | Maltopentose | 8.05 mg/ml |
| | HCl—semicarbazide | 0.4 mg/ml |
| | Triton X-100 | 0.15% |
| | Catalase | 35.2 U/ml |
| | Pyranose oxidase | 54 U/ml |
| | Maltosephosphorylase | 8 U/ml |
| | 50 mM Borax-100 mM KH$_2$PO$_4$ | (pH 6.5) |
| Reagent 2 | 4AA | 0.134 mg/ml |
| | NaN$_3$ | 0.066 mg/ml |
| | Peroxidase | 13.4 U/ml |
| | Triton X-100 | 0.15% |
| | 50 mM Borax-100 mM KH$_2$PO$_4$ | (pH 6.5) |

Procedures

Test tube
    |← 1.5 ml of Reagent 1
Pre-incubation (37° C., 5 min)
    |← 50 μl of Serum sample, Standard serum or Distilled water
Incubation (37° C., 5 min)
    |
Cell
    |← 1.5 ml Reagent 2
Measurement of absorbancy 1 and 5 minutes after the addition of Reagent 2

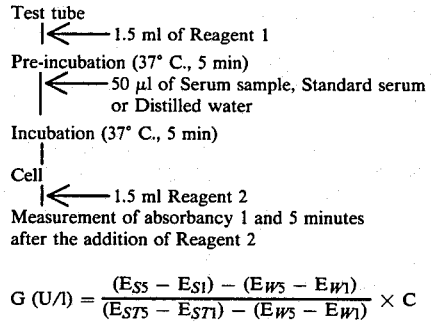

$$G\ (U/l) = \frac{(E_{S5} - E_{S1}) - (E_{W5} - E_{W1})}{(E_{ST5} - E_{ST1}) - (E_{W5} - E_{W1})} \times C$$

G: amylase activity
Results

| | ΔE/min | G (U/l) |
|---|---|---|
| Standard serum | 0.0175 | 470 |
| Sample No. 1 | 0.013 | 349 |
| Sample No. 2 | 0.0076 | 204 |
| Sample No. 3 | 0.0084 | 226 |
| Sample No. 4 | 0.007 | 188 |
| Sample No. 5 | 0.017 | 457 |
| Sample No. 6 | 0.005 | 134 |
| Sample No. 7 | 0.0274 | 736 |
| Sample No. 8 | 0.0112 | 301 |
| Sample No. 9 | 0.0062 | 167 |
| Sample No. 10 | 0.0084 | 226 |

What is claimed is:

1. Pyranose oxidase derived from a microorganism belonging to the genus Coriolus, Daedaleopsis or Gloeophyllum and exhibiting a strong specific activity only on glucose and low activity on sorbose and xylose.

2. A process for producing pyranose oxidase defined in claim 1 which comprises culturing a microorganism belonging to the genus Coriolus, Daedaleopsis or Gloeophyllum which is capable of producing the enzyme in a nutrient medium until enzymatic activity is detected in the culture liquor and thereafter recovering the enzyme therefrom.

3. A process according to claim 2 wherein said microorganism belongs to the species *Coriolus versicolor, Daedaleopsis styracina* or *Gloeophyllum sepiarium*.

4. A process according to claim 2, wherein said microorganism has the identifying characteristics of *Coriolus versicolor* ATCC 20155, *Daedaleopsis styracina* ATCC 20188 or *Gleophyllum sepiarium* NRRL 12506.

5. A process according to claim 2 wherein said culturing is carried out at 20° to 35° C. for 1 to 7 days at about neutral pH.

6. A method for the determination of the substrate for pyranose oxidase in a sample which comprises oxidizing the substrate with pyranose oxidase defined in claim 1, in the presence of oxygen and determining the amount of the reaction product or the amount of oxygen consumed by said reaction.

7. A method according to claim 6 wherein said substrate is glucose.

8. A method according to claim 6 wherein said reaction product is hydrogen peroxide.

9. A method according to claim 7 wherein said glucose is a product of a reaction or decomposition.

10. A method according to claim 6 wherein said enzymatic reaction is carried out in a buffer solution.

11. A method according to claim 8 wherein said hydrogen peroxide is determined by reacting said hydrogen peroxide with a chromogen in the presence of peroxidase to form a pigment and then measuring the amount of pigment formed colorimetrically.

12. A test composition for the determination of a substrate for pyranose oxidase in a sample which comprises a system (A) for oxidizing the substrate with pyranose oxidase defined in claim 1 and a system (B) for determining the amount of said reaction product or the amount of oxygen consumed by said reaction.

13. A test composition according to claim 12 wherein said reaction product is hydrogen peroxide.

14. A test composition according to claim 12 wherein said system (B) comprises peroxidase and a chromogen.

15. A test composition according to claim 14 wherein said chromogen is selected from the group consisting of 4AA-phenol, 4AA-DMA, 4AA-DEA, 4AA-EMAE, 4AA-DBA, 4AA-DHSA, MBTH-phenol, MBTH-DEA and MBTH-DBA.

16. A test composition according to claim 12 wherein said substrate is glucose.

* * * * *